United States Patent [19]
Link

[11] Patent Number: 4,645,506
[45] Date of Patent: Feb. 24, 1987

[54] HIP JOINT ENDOPROSTHESIS WITH A STEM TO BE ANCHORED IN THE FEMUR

[75] Inventor: Helmut D. Link, Hamburg, Fed. Rep. of Germany

[73] Assignee: Waldemar Link GmbH & Co., Hamburg, Fed. Rep. of Germany

[21] Appl. No.: 623,785

[22] Filed: Jun. 22, 1984

[30] Foreign Application Priority Data

Jun. 27, 1983 [DE] Fed. Rep. of Germany ....... 3323131

[51] Int. Cl.$^4$ .............................................. A61F 2/32
[52] U.S. Cl. ..................................................... 623/23
[58] Field of Search ..................... 3/1.9, 1.91, 1.911, 3/1.912, 1.913; 128/92 CA, 92 C, 92 BA, 92 BC; 623/20, 21, 22, 23, 16, 17, 18

[56] References Cited

FOREIGN PATENT DOCUMENTS

| 0041591 | 2/1981 | European Pat. Off. ............. 3/1.912 |
| 2839092 | 3/1980 | Fed. Rep. of Germany . |
| 0085147 | 11/1982 | Fed. Rep. of Germany . |
| 817525 | 7/1959 | France . |
| 1278359 | 1/1961 | France . |
| 2419717 | 11/1978 | France . |

Primary Examiner—Richard J. Apley
Assistant Examiner—David Isabella
Attorney, Agent, or Firm—Handel & Morofsky

[57] ABSTRACT

A hip joint endoprosthesis has a downward tapering stem (1) which is to be anchored in the femur and is composed of a main part (7) connected to the condyle head (4) and of a plurality of wedge pieces (10) which are movably guided longitudinally along the main part by means of cooperating guide surfaces (11,12). The friction on the guide surfaces between the main part (7) and the wedge pieces (10) is smaller than the friction caused by the outer surface (13), formed for promoting adhesion, of wedge pieces (10) on the bone. When the medullary cavity receiving the prosthesis stem widens, the load on the main part (7) causes an expansion of the wedge pieces (10) and hence an adaptation of the shape of the prosthesis.

11 Claims, 5 Drawing Figures

HIP JOINT ENDOPROSTHESIS WITH A STEM TO BE ANCHORED IN THE FEMUR

DESCRIPTION

The invention relates to a hip joint endoprosthesis with a downward-tapering stem which is to be anchored in the femur and which is composed of a main part connected to the condyle head and of a wedge piece which is movably guided longitudinally along the main part by means of cooperating guide surfaces and has an outer surface formed for promoting adhesion to the bone tissue.

In a prosthesis, of the type set out, which is not part of the previously published state of the art (EU-A No. 85,147), the wedge piece is provided on the lateral side of the main part of the stem. In order to ensure a functionally correct position of the condyle head of the prosthesis, the main part of the stem, carrying the condyle head, is first knocked into the bone. Subsequently, the wedge piece is knocked in while firmly holding the main part of the stem, the wedge shape of the wedge piece effecting jamming of the stem in the bone, without altering the height position of the main part of the stem in the bone. If the stem becomes loose, for example due to unphysiological loading or due to ageing phenomena, this can be corrected by knocking the wedge piece further in at a later date during a re-operation. In any case, it is envisaged with this prosthesis that the main part of the stem assumes and retains a predetermined height relative to the bone and only the wedge action of the wedge piece is utilized by knocking it in for jamming the prosthesis in the bone tube. The known prosthesis does not exclude the possibility that the prosthesis becomes loose due to widening of the bone receiving the stem, and a reoperation is certainly necessary in order to eliminate the loosening, by knocking the wedge piece further.

By contrast, it is the object of the invention to provide an endoprosthesis of the type initially set out, which has a lesser tendency to loosen or none at all even when the medullary canal receiving the prosthesis stem widens.

The object is achieved according to the invention when a plurality of wedge pieces is provided on stem sides facing away from one another and the guide surfaces, converging in the manner of a wedge, are formed to produce an adhesive force which is lower than that of the outer surfaces of the wedge pieces.

The prosthesis according to the invention differs in principle from the known prosthesis in that the wedge pieces as a rule have a height in the bone, which is fixed once and for all by the operation, whilst the main part of the stem carrying the condyle head is displaceable in the longitudinal direction, in fact automatically due to the natural load which tends to push the main part of the stem further into the bone, between the wedge pieces. Any widening of the bone tube is in this way automatically compensated by an expansion of the wedge pieces with corresponding lowering of the main part of the prosthesis stem. Admittedly, this also involves a lowering of the condyle head, but the physiological conditions are only slightly altered as a result, and an appropriate choice of the wedge angle, formed by the main part of the stem between the guide surfaces of the wedge pieces, can ensure that, even with the greatest conceivable widening of the medullary canal, the lowering distance of the condyle head remains within the tolerance limits.

The self-adjusting effect of the prosthesis according to the invention is made possible by the fact that the adhesion of the outer surfaces of the wedge pieces to the bone tissue is greater than the adhesion which acts in the cooperating guide surfaces of the main part of the stem and of the wedge pieces. An expert is familiar with many possibilities of forming the surface of a prosthesis stem in such a way that adhesion to the bone tissue is promoted, for example by elevations and recesses, surface porosity and perforations into which the bone tissue grows.

He is also familiar with possibilities for predetermining the adhesive force acting between the guide surfaces, for example by means of surface roughness or by providing the surfaces with wedge-shaped cross-sections.

The effect of the invention is tied to the wedge-shaped design of the main part of the stem between the guide surfaces. A wedge-shaped design of the wedge pieces is advantageous but not absolutely necessary for this purpose. Rather, it is conceivable that the guide surfaces provided on the wedge pieces run parallel to the outer surfaces thereof in longitudinal section or that the wedge pieces even taper from the distal end to the proximal end, so that the wedge angle effective on the guide surfaces is greater than the natural wedge angle of the medullary canal, widening in the proximal direction, of the femur.

Although it is possible to allow the peripheral surface of the prosthesis stem, interacting with the bone tissue, in the upper section thereof to be formed exclusively by the wedge pieces, it is in general more advantageous when, in addition to the wedge pieces, the main part of the prosthesis stem also participates in the formation of the peripheral surface. This ensures that normally, as long as there is no widening of the medullary canal, the anchoring forces are, entirely or for a substantial part, transmitted by the surface of the main part of the stem to the bone, so that a wedging movement can take place only when the surface of the main part of the prosthesis stem looses contact with the bone tissue, due to widening of the bone tube, and thus sinks more deeply into the medullary cavity, until the arrangement obtains a hold again as a result of expansion of the wedge pieces. In a particularly advantageous embodiment, for example, a plurality of ribs integral with the stem project from the main part of the stem to the peripheral surface and the wedge pieces are arranged in the interspaces between the ribs.

To enable the said transmission of force from the main part of the stem to the bone tissue to take place, the stem advantageously also has a surface structure which is formed to promote adhesion relative to the bone tissue, and, according to a further feature of the invention, even the surface, interacting with the bone tissue, of the main part of the stem can be sized to be adequate for transmitting, by itself, the load. The intended effect is that not every strong load on the prosthesis leads to a relative movement of the prosthesis stem in relation to the wedge pieces and the bone tissue. Rather, it is the aim to allow this correction movement to take place only when the bond between the main part of the prosthesis stem and the bone tissue deteriorates. This bond can make a contribution to ensuring that the correction movement does not take place traumatically as a sudden fracture phenomenon under a peak load, but is a continuous rearrangement process, in which there is an equilibrium between the forces transmitted by the wedge pieces and the forces transmitted directly from the main part to the bone tissue.

According to a further feature of the invention, it can be provided that the wedge angle is smaller than the angle of friction so that, on the one hand, the desired expansion of the wedge pieces for the purpose of compensating a widening of the medullary canal can take place as a result of a load on the prosthesis and, on the other hand, the elastic resilient tendency of the bone tissue cannot lead to the opposite relative movement, which otherwise could entail continuous "pumping" of the arrangement. One means for preventing such a continuous alternating movement is to design the cooperating guide surfaces for intensive friction. Only those forces which exceed the frictional force can then cause a relative movement.

Particularly advantageous is the embodiment of the guide surfaces, formed for intensive friction, in the shape of a stepping or serration, which is made in such a way that jumping of the parts from one engaged position into the next is only possible when a certain force threshold is exceeded. In the case of stepping in the form of a multiplicity of individual steps, these are each composed of a surface of large wedge angle (angle between this surface and the longitudinal direction of the stem) and a further surface which, with the longitudinal direction of the stem, encloses an angle which is very small, zero or negative (an angle opening downwards). The loading forces acting in the longitudinal direction of the stem are thus transmitted via the step surfaces of large wedge angle and, at the same time, the wedge pieces are subjected to an expanding force which is equal to the quotient of the loading forces divided by the tangent of the wedge angle. A relative movement then takes place only when the expanding forces become larger than those forces of the bone tissue which counteract the expansion, in the case of an extension by the radial height of a step. The expanding force to be absorbed by the bone tissue can be limited by selecting a large wedge angle. By suitable sizing of the radial step height (measured transversely to the direction of the stem), that degree of medullary canal widening is determined at which a correction jump of the prosthesis parts is to take place in each case. The wedge angle and the step height are advantageously sized such that the step height is not larger, or not substantially larger, than the extension of the bone tissue to be expected, on the basis of the wedge angle, under maximum loading.

In general, the invention presupposes that the prosthesis stem is inserted without cement or with very little cement.

The invention is explained below in more detail by reference to the drawing which illustrates an advantageous exemplary embodiment and in which.

Figure 1:
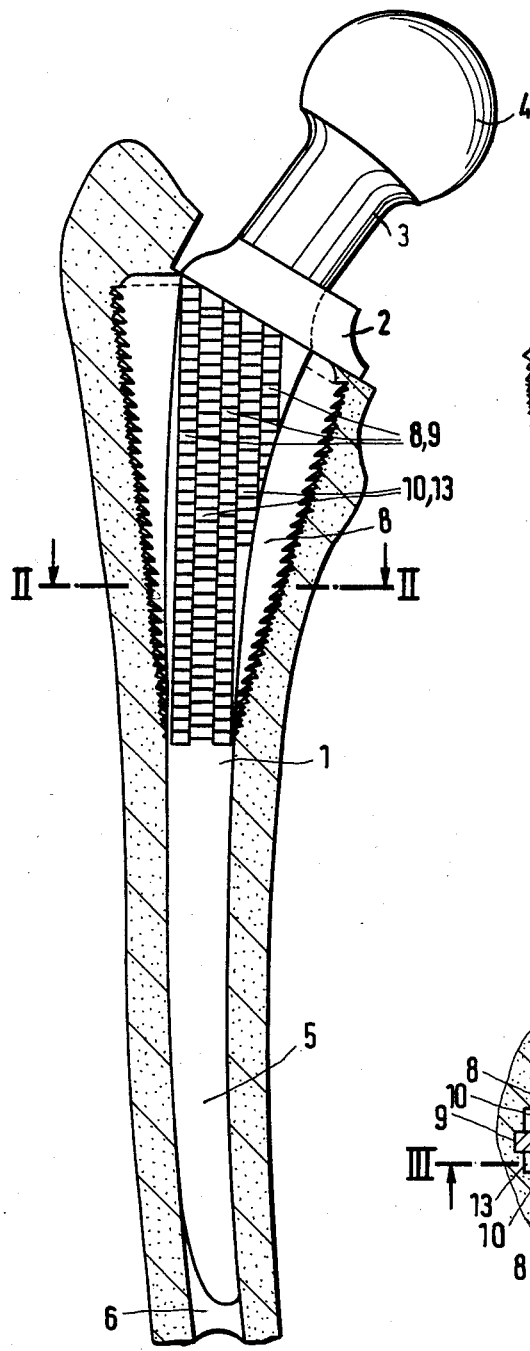
FIG. 1 shows a side view of a hip joint-femur stem prosthesis.

The prosthesis consists of the stem 1, the collar 2 which may be exchangeable, the neck 3 of the head and the condyle head 4. In its lower part 5, the stem 1 is shaped conventionally, in such a way that its surface can substantially be in contact with the hard cortex layer of the femur bone. In the upper region, where the medullary canal 6 greatly widens towards the trochanter region, ribs 8 which extend in the longitudinal direction of the stem and are rigidly joined to the main part 7, start from the main part 7. Three such ribs 8 of cross-sectionally parallel arrangement are provided in each case on the front and rear of the stem. Two ribs are arranged on the inside and one rib is arranged on the outside. The ridges of the ribs 8, that is to say those facing outwards, are provided with teeth 9, so that they can be more securely anchored in the bone tissue. Other surface shapes which ensure good bonding to the bone tissue can also take the place of the teeth.

Between two ribs 8 joined to the main part 7, there is in each case an interspace of constant width, which forms in each case a guide for a wedge piece 10 which is movable in the longitudinal direction of the stem between the ribs fixed to the stem and is supported by its guide surface 12 on the bottom 11, forming the guide surfaces, of the interspace between the ribs. On its rear surface, it has teeth 13 for more secure anchorage in the bone tissue, or it has an alternative surface shape. In the example shown, the serration 9 of the ribs rigidly joined to the main part 7 is made in the form of saw teeth in such a way that it offers a resistance to a sinking relative movement which is less than that of the serration 13 of the movable stem parts. However, this is not absolutely necessary.

The distance between mutually opposite guide surfaces 11 on the different sides of the main part increases from the bottom upwards. This means that they form wedge surfaces, by means of which the wedge pieces 10 are urged outwards when the stem sinks deeper into the medullary cavity and are thus forced into stronger adhesion to the bone tissue and therefore do not share this sinking movement. It can be seen in the longitudinal section of FIG. 4 that the wedge angle 14 enclosed by the guide surfaces 11 with the longitudinal direction of the stem is very small. This means that the wedge pieces 10 virtually do not participate in the transmission of the longitudinal forces from the stem to the bone. However, they take a full part in transmitting forces which act transversely to the longitudinal direction of the stem, and are therefore capable of ensuring the fixing of the stem in the medullary cavity, even if the latter widens. It need not be feared that a continuous to-and-fro movement of the movable and fixed stem parts relative to one another in the longitudinal direction will take place, when the prosthesis is subjected to alternating loads. The reason is that the extremely small wedge angle is in every case smaller than the angle of friction, so that alternating transverse forces cannot cause a longitudinal displacement of the wedge pieces.

Figure 4:
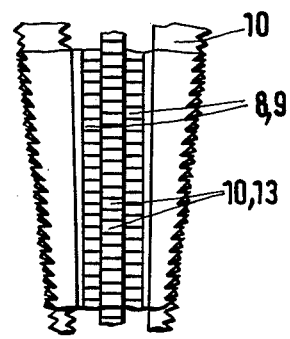
FIG. 4 shows a partial side view in the direction of projection perpendicular to that in FIG. 1.
Figure 2:
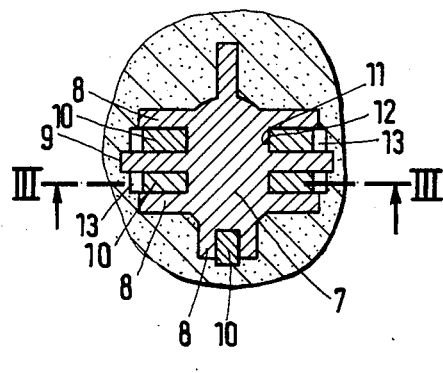
FIG. 2 shows a cross-section through the stem along the line II—II in FIG. 1.
Figure 3:
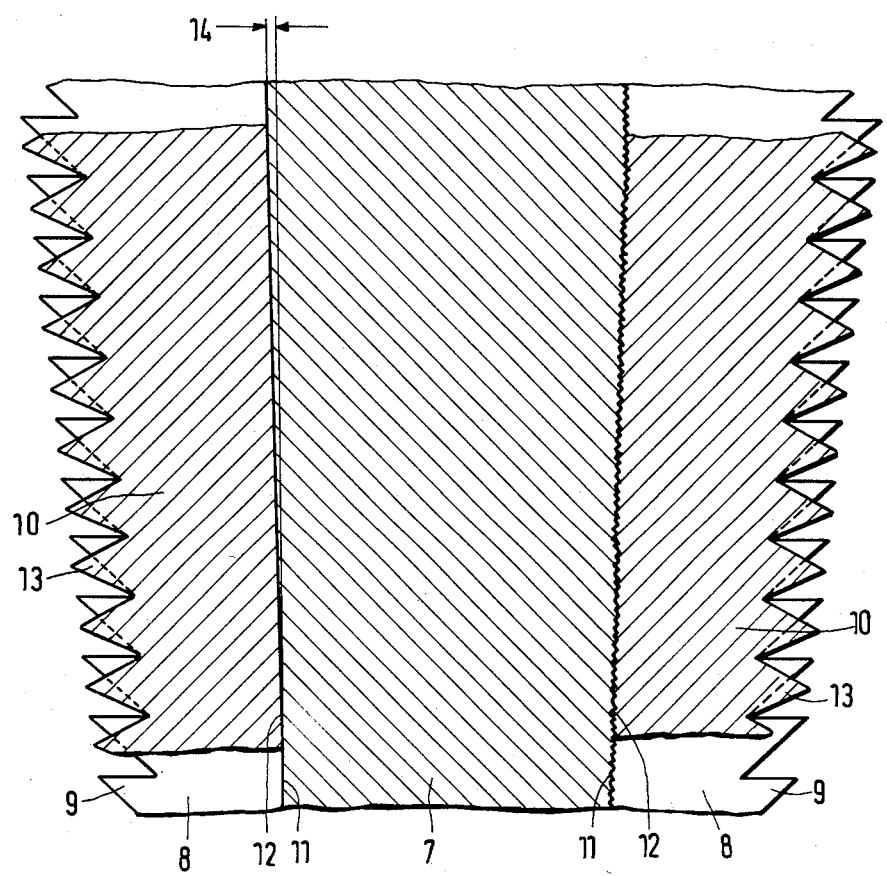
FIG. 3 shows a longitudinal section on a larger scale along the line III—III in FIG. 2, in particular with a different design of the guide surfaces on the left-hand and right-hand sides of the center line.

FIG. 4 shows, in the left-hand half, the smooth version of the pair of guide surfaces 11, 12 and, on the right-hand side, a serrated version which is intended to prevent alternating longitudinal forces from causing varying displacements between the fixed and movable parts of the prosthesis, as long as the displacements remain below a certain threshold.

Figure 5:
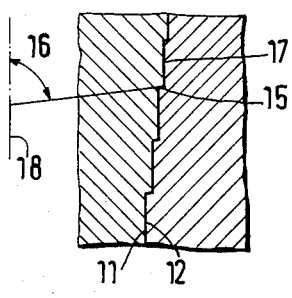
FIG. 5 shows a stepped design of the guide surfaces.

FIG. 5 shows a stepped version of the guide surfaces 11 and 12, each step being composed of a surface 15 of large wedge angle 16 and of another surface 17 which extends approximately parallel to the longitudinal direction 18 of the shaft. It is possible to give different shapes to the various pairs of guide surfaces on one and the same prosthesis. However, identical shaping of all the guide surfaces is preferred.

On the (lateral) outside of the prosthesis shown, a rib rigidly joined to the main part of the stem is provided instead of a movable wedge piece, because, in that area, tensile forces are to be transmitted rather than compressive forces.

I claim:

1. A hip joint endoprosthesis, comprising:
   (a) a downward-tapering stem having medial, lateral, anterior and posterior surface portions, and configured and dimensioned to have outer surfaces which are disposed against and anchored in a femur, said stem comprising:
     (i) a downward tapering main part having a predetermined length; and
     (ii) a condyle head connected to said main part;
   (b) a plurality of wedge pieces, said wedge pieces being provided on sides of said stem facing away from one another;
   (c) guide means disposed on the opposing surface portions of said main part and configured to mate with and guide said wedge pieces for lengthwise movement along said main part and to prevent movement perpendicular to said lengthwise movement, said guide means having a converging portion which converges in the manner of a wedge at a wedge angle;
   (d) gripping surfaces disposed on each of said wedge pieces and formed for promoting adhesion to the inside of the femur; and
   (e) gripping means disposed on a portion of said guide means which forms said outer surfaces for producing an adhesive force against the inside of the femur.

2. A hip joint endoprosthesis, comprising:
   (a) a downward-tapering stem configured and dimensioned to have medial, lateral, anterior, and posterior surface portions and to be anchored in a femur, said stem comprising:
     (i) a downward-tapering main part having a predetermined length; and
     (ii) a condyle head connected to said main part;
   (b) a plurality of wedge pieces, said wedge pieces being provided with inside surfaces which bear against sides of said stem facing away from one another, and formed to substantially fill the gap between the inside of said femur and said sides of said stem;
   (c) guide members defining guide surfaces disposed on the opposing surface portions of said main part and configured to mate with and guide said wedge pieces for lengthwise movement along said main part and to prevent movement perpendicular to said lengthwise movement, said guide surfaces having a portion which converges in the manner of a wedge at a wedge angle; and
   (d) gripping surfaces disposed on each of said wedge pieces and formed for promoting adhesion to the inside of the femur, said guide members cooperating with the inside surfaces of said wedge pieces and being configured to produce a mechanical resistance with respect to the wedge pieces which is less than the mechanical resistance between the gripping surfaces and the inside of said femur.

3. A hip joint endoprosthesis as claimed in claim 2, wherein the gripping surfaces and a portion of said main part of said stem both engage the inside of the femur.

4. A hip joint endoprosthesis as claimed in claim 2, wherein said main part has outer surfaces which face the femur tissue and have an irregular surface structure which promotes mechanical gripping.

5. A hip joint endoprosthesis as claimed in claim 4, wherein said portion of said main part which engages the inside of the femur has an area large enough with respect to the inside area of the femur to transmit normal physiological loads on the prosthesis without damage to the femur.

6. A hip joint endoprosthesis comprising:
   (a) a downward-tapering stem configured and dimensioned to having medial, lateral, anterior, and posterior surface portions and to be anchored in a femur, said stem comprising:
     (i) a downward-tapering main part having a predetermined length; and
     (ii) a condyle head connected to said main part;
   (b) a plurality of wedge pieces, said wedge pieces being provided with inside surfaces which bear against sides of said stem facing away from one another, and formed to substantially fill the gap between the inside of said femur and said sides of said stem;
   (c) guide members defining guide surfaces disposed on the opposing surface portions of said main part and configured to mate with and guide said wedge pieces for lengthwise movement along said main part, said guide surfaces having a portion which converges in the manner of a wedge at a wedge angle, said guide members further comprising a plurality of wedged-shaped interspaced ribs which are rigidly joined to said main part and have outer surfaces which form part of the outer surface of the stem and project outwardly against the inside of the femur and the wedge pieces are positioned in the interspaces between the ribs; and
   (d) gripping surfaces disposed on each of said wedge pieces and formed for promoting adhesion to the inside of the femur, said guide members cooperating with the inside surfaces of said wedge pieces and being configured to produce a mechanical resistance with respect to the wedge pieces which is less than the mechanical resistance between the gripping surfaces and the inside of said femur.

7. A hip joint endoprosthesis as claimed in claim 6, wherein the cooperating guide surfaces are configured irregularly to cause intensive friction.

8. A hip joint endoprosthesis as claimed in claim 7, wherein the guide surfaces against which said wedge pieces bear are serrated.

9. A hip joint endoprosthesis as claimed in claim 7, wherein the guide surfaces against which said wedge pieces bear are stepped.

10. A hip joint endoprosthesis as claimed in claim 9, wherein a multiplicity of wedge surface steps is provided, which are each composed of a surface of large wedge angle and of a surface of small wedge angle.

11. A hip joint endoprosthesis as claimed in claim 2, wherein said wedge angle is smaller than the angle of friction.

* * * * *